United States Patent [19]

Nelson, Jr.

[11] Patent Number: 5,318,530
[45] Date of Patent: Jun. 7, 1994

[54] GASTROINTESTINAL TUBE WITH INFLATABLE BOLUS

[75] Inventor: Richard L. Nelson, Jr., Wilmette, Ill.

[73] Assignee: Bissel Medical Products, Inc., Naperville, Ill.

[21] Appl. No.: 803,029

[22] Filed: Dec. 6, 1991

[51] Int. Cl.$^5$ .......................................... A61M 25/00
[52] U.S. Cl. ................................. 604/96; 604/45; 604/49; 604/164; 604/270; 604/280
[58] Field of Search ............... 604/35, 43, 45, 49, 604/54, 95, 96, 102, 129, 164, 170, 264, 268, 270, 280

[56] References Cited

U.S. PATENT DOCUMENTS

| | | | |
|---|---|---|---|
| 1,207,479 | 12/1916 | Bisgaard . | |
| 1,736,182 | 11/1929 | Wilkins . | |
| 2,799,273 | 7/1957 | Oddo | 128/325 |
| 3,395,710 | 8/1968 | Stratton et al. | 128/350 |
| 3,941,119 | 3/1976 | Corrales | 128/2 M |
| 3,948,272 | 4/1976 | Guibor | 128/350 |
| 4,180,076 | 12/1979 | Betancourt | 604/102 |
| 4,270,542 | 6/1981 | Plumley | 128/350 |
| 4,364,394 | 12/1982 | Wilkinson | 604/35 |
| 4,368,739 | 1/1983 | Nelson, Jr. | 604/54 |
| 4,516,970 | 5/1985 | Kaufman et al. | 604/270 |
| 4,543,089 | 9/1985 | Moss | 604/93 |
| 4,654,036 | 3/1987 | Tolkoff | 604/270 |
| 4,676,778 | 6/1987 | Nelson, Jr. | 604/45 |
| 4,704,111 | 11/1987 | Moss | 604/270 |
| 4,769,014 | 9/1988 | Russo | 604/270 |
| 4,795,430 | 1/1989 | Quinn et al. | 604/97 |
| 4,863,424 | 9/1989 | Blake, III et al. | 604/270 |
| 4,900,306 | 2/1990 | Quinn et al. | 604/97 |
| 4,925,446 | 5/1990 | Garay et al. | 604/96 |
| 4,973,305 | 11/1990 | Goltzer | 604/51 |
| 5,015,232 | 5/1991 | Maglinte | 604/43 |
| 5,037,387 | 8/1991 | Quinn et al. | 604/270 |
| 5,078,701 | 1/1992 | Grassi et al. | 604/264 |
| 5,112,310 | 5/1992 | Grobe | 604/96 |

FOREIGN PATENT DOCUMENTS 2934628 3/1981 Fed. Rep. of Germany ...... 604/270
1139442A 9/1981 U.S.S.R. .

OTHER PUBLICATIONS

"A Double-Lumened Plastic Tube for Intestinal Intubation", Honor et al., reprint of Archives of Surgery, Oct. 1947, vol. 55 pp. 498–504.
*Techniques of Percutaneous Gastrostomy,* Ponsky, Jeffrey L., Chapter 4, pp. 21–32.
*Introduction and Endoscopic Positioning of the Miller-Abbott Probe in Treating Occlusive Intestinal Syndromes.*

Primary Examiner—John D. Yasko
Assistant Examiner—Anthony Gutowski
Attorney, Agent, or Firm—Marshall, O'Toole, Gerstein, Murray & Borun

[57] ABSTRACT

An intestinal catheter is inserted into the gastrointestinal tract by use of an endoscope or a guidewire in combination with an inflatable bolus and performs the functions of aspirating the stomach and feeding the small intestine. The inflatable bolus may be filled with a heavy liquid such as water so that the downstream end of the catheter is moved through the gastrointestinal tract by peristalsis.

18 Claims, 7 Drawing Sheets

GASTROINTESTINAL TUBE WITH INFLATABLE BOLUS

BACKGROUND OF THE INVENTION

The present invention relates generally to intestinal catheters, and more particularly to an intestinal catheter, inserted by use of an endoscope or a guidewire in combination with a bolus, for the purpose of aspirating the contents of the stomach and delivering feeding solutions to the small intestine.

The gastrointestinal tract comprises, in descending order from the mouth or nose, the esophagus, the stomach, the small intestine and the large intestine. The small intestine or bowel comprises, in descending order, the duodenum, connected to the stomach through an opening called the pylorus, the jejunum, which connects with the duodenum at a location identified by an adjacent ligament called the Ligament of Treitz, and the ileum, which in turn connects with the large bowel.

It is often desirable to emplace within the gastrointestinal tract a catheter where the downstream end of the catheter is located in the small intestine. Nelson, U.S. Pat. No. 4,676,778 and Nelson, U.S. Pat. No. 4,368,739 describe devices which can be emplaced within the small intestine. Those devices are designed to be inserted during surgery and are provided with pairs of inflatable balloons which facilitate the manipulation of the catheter through the small intestine. Because those devices require manual manipulation of the intestinal tract, they are inserted only during surgery.

There are techniques for insertion of intestinal catheters which do not involve surgery. Single lumen feeding tubes have been inserted into the intestine by use of an endoscope which attaches to a thread or cord at the downstream end of the catheter. Such catheters have sometimes been equipped with a weight or bolus portion in the catheter and are described in Russo, U.S. Pat. No. 4,769,014.

Another technique for insertion of a catheter into the intestine is by use of a guidewire. The guidewire is inserted into the tube for the purpose of adding rigidity and directional memory to the tube, and the tube and guidewire are inserted into the gastrointestinal tract. The catheter and guidewire move through the gastrointestinal tract by manipulating the guidewire at the upstream or operator end of the tube. A radiologist uses a fluoroscope to determine the position of the guidewire and catheter and to aid in moving them further through the gastrointestinal tract.

In the past, use of an endoscope or guidewire to emplace a catheter deep into the small intestine is not always satisfactory. The tight curves in the small intestine make maneuvering a catheter difficult either with an endoscope or with a guidewire. Moreover there is a need for a simple method of replacing a catheter which has been previously emplaced by use of an endoscope or a guidewire.

SUMMARY OF THE INVENTION

There is provided in accordance with the present invention a single tube or catheter which performs the dual functions of aspirating the contents of the stomach and delivering feeding liquid into the small intestine for nourishing the patient. The catheter can be inserted nasally into the stomach or by a gastrostomy, a procedure where an opening is made through a patient's skin into the stomach. A gastrostomy can be accomplished surgically through an abdominal incision or, using a gastroscope, percutaneously by inserting a sharp pointed object, such as a needle or stilette, through the skin and directly into the stomach. The catheter of the present invention can be emplaced by use of an endoscope or with a guidewire, is easily replaced by a new catheter and can also serve to easily replace a previously emplaced catheter.

The catheter comprises a flexible tube having upstream and downstream ends. The tube has one or more short lengths of silk suture material resembling whiskers attached to its downstream end which are capable of being grasped by the forceps of an endoscope while emplacing the catheter in the gastrointestinal tract. The catheter has an inflatable bolus near the downstream end of the tube. When the bolus is inflated with a liquid such as water, its weight and volume will aid peristalsis in propelling the catheter further into the gastrointestinal tract. Peristalsis is the wave-like muscular contractions that move food or other matter through the intestines. The bolus also serves as a means for preventing withdrawal of the catheter when an endoscope or guidewire is removed from a patient's gastrointestinal tract.

The tube has four lumens: a first lumen for feeding, a second lumen for suction, a third lumen which serves to vent the suction lumen and a fourth lumen which serves to inflate and deflate the bolus. Near the upstream end of the tube is a fitting for connecting the suction lumen to suction, a fitting for connecting the feeding lumen to a source of nutritive or medicinal material, a structure for venting the vent lumen to atmosphere and a fitting for connecting the bolus lumen to a source of fluid for inflating the bolus.

The tip of the downstream end of the tube has an opening. The tip opening is connected to the feeding lumen and allows feeding material to exit the tube and flow into the small intestine. The tip opening and feeding lumen also function to accept a guidewire for insertion or removal of the catheter from the gastrointestinal tract.

A plurality of gastric openings are located in the wall of the tube near the middle of the catheter. These gastric openings are connected to the suction lumen and allow liquid and gaseous material to be aspirated from the stomach.

A channel connects the vent lumen with the suction lumen. The channel is located downstream of the most downstream of the gastric openings. The channel allows air to enter the suction lumen to prevent clogging of the suction lumen when the stomach is being aspirated.

The tube has a radio-opaque stripe along its entire length, and the downstream end of the tube is coated with a radio-opaque material. These radio-opaque features can be viewed by a radiologist through a fluoroscope to determine whether a catheter has been properly emplaced within the gastrointestinal tract.

The tube is emplaced within the gastrointestinal tract by a variety of procedures. In one procedure, the catheter and an endoscope are introduced together into the patient. The forceps within the endoscope then grasp a whisker on the downstream end of the catheter and pull the catheter into the gastrointestinal tract until the downstream tip is at a desired location. In a second procedure, the catheter is pulled by the forceps within the endoscope into the gastrointestinal tract short of the desired location. The bolus is then inflated and the endoscope releases the whisker and is removed from the patient. The weight of the bolus in combination with peristalsis carries the catheter further into the intestine to the desired location.

In a third procedure, a guidewire is inserted into the feeding lumen and, using the shape and rigidity of the guidewire stented catheter, the catheter is inserted into the patient's gastrointestinal tract short of its desired location. The bolus is then inflated and the guidewire removed from the catheter. The weight of the bolus in combination with peristalsis moves the catheter further into the patient's intestine to the desired location.

In another procedure, as for instance replacing an old or damaged catheter, a guidewire can be inserted all the way into a previously emplaced catheter and held in place in the gastrointestinal tract, while the previously emplaced catheter is removed over the guidewire. The upstream end of the emplaced guidewire remains outside the patient's body and this end is then inserted through the tip opening of a fresh, unemplaced catheter and into the feeding lumen. The catheter is then advanced over the guidewire until the downstream end of the catheter reaches the tip of the guidewire. The catheter can be inserted further into the gastrointestinal tract by viewing the guidewire and catheter through a fluoroscope and manipulating the upstream end of the wire, or by inflating the bolus allowing peristalsis to move the catheter.

Other features and advantages are inherent in the catheter claimed and disclosed or would become apparent to those skilled in the art from the following detailed description in conjunction with the accompanying diagrammatic drawings.

DETAILED DESCRIPTION

Figures 1, 2, 3:
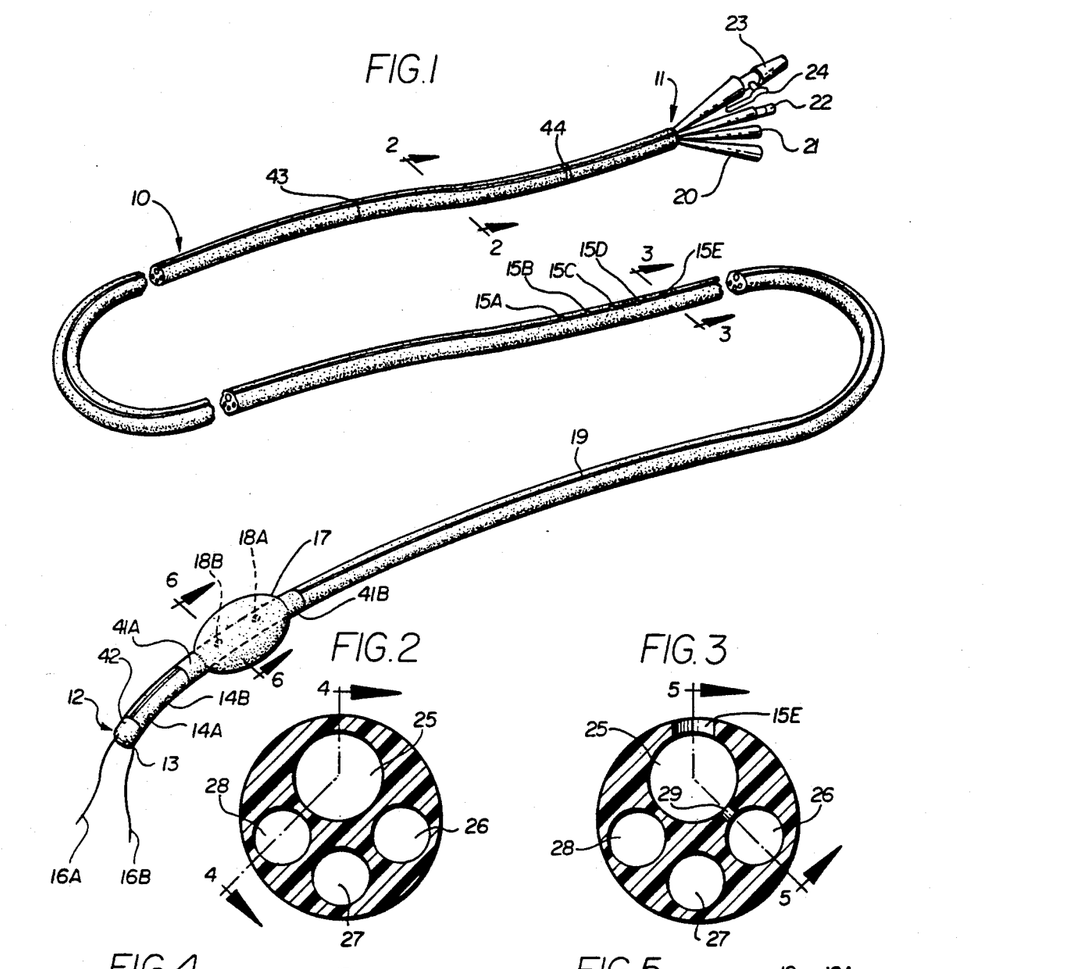
FIG. 1 is a perspective of an embodiment of a catheter constructed in accordance with the present invention.
FIG. 2 is a sectional view taken along line 2—2 in FIG. 1.
FIG. 3 is a sectional view taken along line 3—3 in FIG. 1.

Referring initially to FIG. 1, there is illustrated a catheter constructed in accordance with an embodiment of the present invention and comprising a flexible tube indicated generally at 10, having an upstream end indicated generally at 11 and a downstream end indicated generally at 12. The tube may be made out of any suitable material, including polyurethane or polyvinylchloride.

Figures 6, 7:
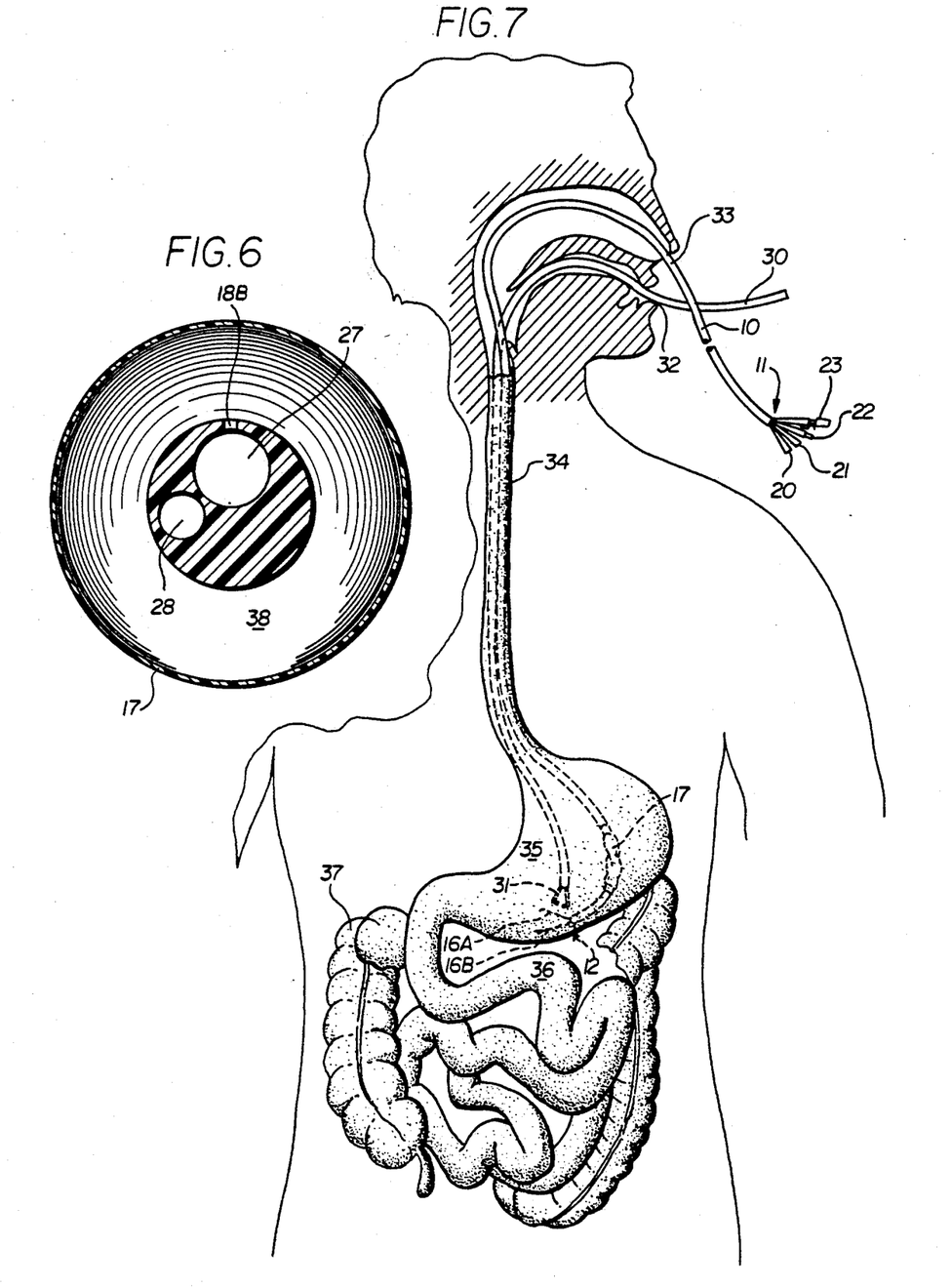
FIG. 6 is a sectional view taken along line 6—6 in FIG. 1.
FIG. 7 is a perspective of a human torso, partially cut away, showing a catheter constructed in accordance with the present invention and emplaced within the gastrointestinal tract through the nose.

Near downstream end 12 is an inflatable bolus 17. In FIGS. 1 and 6, bolus 17 is depicted as fully inflated. Bolus 17 is made of any strong resilient material such as urethane. The bolus is attached to tube 10 by bolus cuffs 41A-B. Bolus cuffs 41A-B are glued, adhered or formed integral with tube 10. Bolus 17 has a center (not depicted) which is located midway between cuff 41A and cuff 41B. The center of bolus 17 is preferably located approximately 1 5/16 inches (3.3 cm) from downstream end 12. The length of bolus 17, defined as the distance between cuff 41A and 41B, is preferably approximately 1 inch (2.54 cm). The diameter of bolus 17 at its center is preferably about ¾ inch (1.9 cm) when inflated.

One or more whiskers 16A-16B are located at downstream end 12. In the embodiments depicted in the drawings there are two whiskers 16A-16B. Whiskers 16A-16B may be made of any strong, thin, flexible material such as suture thread and are preferably 8 cm in length. The sutures must be thick enough and long enough to be grasped by the forceps of an endoscope (FIGS. 7-12) and must be strong enough so that they do not break when being pulled by endoscope forceps 31 (FIGS. 7 and 10) through the gastrointestinal tract. The whiskers are preferably located off to one side of the tube rather than extending directly out from the central axis (not depicted) of the tube.

Figure 4:
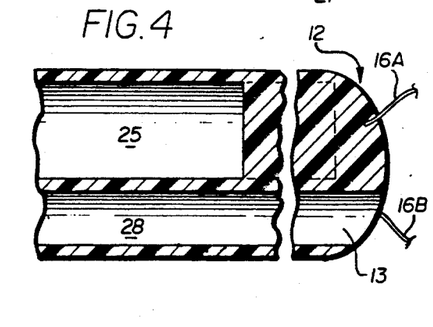
FIG. 4 is a sectional view taken along line 4—4 in FIG. 2.

Located within tube 10 (FIGS. 2-6) is suction lumen 25, vent lumen 26, bolus lumen 27 and feeding lumen 28. At the tube's downstream end 12 is a tip opening 13 communicating with feeding lumen 28 (FIG. 4). At upstream end 11 is a fitting 20 for connecting feeding lumen 28 to a source of nutritive or medicinal material (FIG. 1). When the catheter is emplaced within the gastrointestinal tract, feeding material enters fitting 20 and passes through feeding lumen 28 to tip opening 13 from where it enters the small intestine. Tube 10 may have additional feeding lumen openings 14A-14B near downstream end 12 which also communicate with feeding lumen 28, in order to provide additional avenues for feeding material to enter the small intestine. Feeding lumen openings 14A-14B and tip opening 13 are preferably located downstream of bolus 17 so that fluid entering the intestine through the catheter enters downstream of the bolus.

Figure 5:
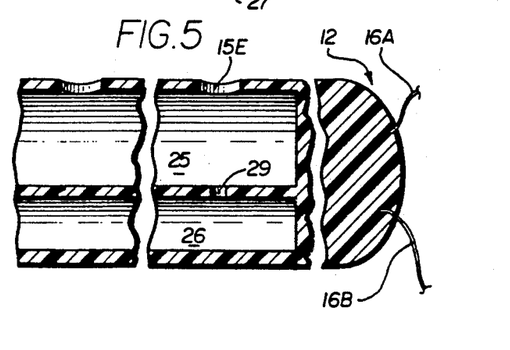
FIG. 5 is a sectional view taken along line 5—5 in FIG. 3.

Near the middle of the tube are gastric openings 15A-E. Each gastric opening 15A-15E communicates with suction lumen 25 (FIGS. 3 and 5). The tube has length such that when downstream end 12 is in the small intestine, at least some of gastric openings 15A-15E are in the stomach. At the upstream end of the tube is a suction connection fitting 23 (FIG. 1) for connecting suction lumen 25 to a suction source, and a suction control element 24.

Vent lumen 26 is connected to suction lumen 25 by a vent channel 29 (FIGS. 3 and 5). Vent channel 29 is located at or downstream of the furthest downstream of the gastric openings 15A-15E. In the embodiment of the invention depicted in FIGS. 1-5, channel 29 is adjacent to gastric opening 15E. At the tube's upstream end 11 is a vent fitting 21 for connecting vent lumen 25 with the atmosphere (FIG. 1). Channel 29, vent lumen 26 and vent fitting 21 together comprise structure for preventing plugging of gastric openings 15A-E by the lining of the stomach when the stomach is being aspirated. Absent some preventative expedient, the stomach lining can be sucked up against the gastric openings 15A-E and plug them. Because catheter 10 includes channel 29, vent lumen 26 and vent fitting 21, continuous suction can be employed through lumen 25 without manually interrupting the suction or without employing a complicated automatic suction interrupting valve, and there will be no plugging of gastric openings 15A-E by the lining of the stomach.

Suction lumen 25 and vent lumen 26 serve no purpose downstream of vent channel 29. Therefore, in the embodiment of the invention depicted, those lumens have been plugged or terminate just downstream of vent channel 29 (FIG. 5).

Located between cuff 41A and cuff 41B are bolus openings 18A-18B. Bolus openings 18A-18B communicate with the interior 38 of bolus 17 and with bolus lumen 27 (FIG. 6). At upstream end 11 is bolus fitting 22 which communicates with bolus lumen 27. Bolus fitting 22 is constructed to attach to a source of fluid (not depicted). Bolus fitting 22, bolus lumen 27 and bolus openings 18A-B comprise structure for inflating or deflating bolus 17.

The catheter depicted in FIG. 1 has a radio-opaque stripe 19 on the exterior surface of the tube, running from downstream end 12 to upstream end 11. Radio-opaque stripe 19 is comprised of a material which can be viewed through a fluoroscope when the catheter has been emplaced in the patient's body. Radio-opaque stripe 19 may be attached to the exterior surface of tube 10 or may be embedded within the tube. Gastric openings 15A-15E are located on an area of the exterior surface of tube 10 in line with radio-opaque stripe 19. When viewed under a fluoroscope, gastric openings 15A-F appear as gaps in the radio-opaque stripe. Radio-opaque stripe 19 serves as a means of determining the location of the catheter in the patient's gastrointestinal tract. The gaps in radio-opaque stripe 19, caused by gastric openings 15A-15E, aid in indicating whether those openings are properly located within the patient's stomach.

The catheter also has a radio-opaque area 42 located at the tube's downstream end 12. Radio-opaque area 42 aids in determining the location of the downstream portion of the catheter within a patient's gastrointestinal tract so that it can be properly positioned in the small intestine.

The catheter may also have a first marking 43 and a second marking 44 on the surface of the tube serving as indications of the extent to which the catheter should be inserted. If the catheter is to be inserted nasogastrically, first marking 43 is preferably located about 17½ inches (44.5 cm) upstream of the most upstream gastric opening 15A. Second marking 44 is preferably located about 5 inches (12.7 cm) further upstream of first marking 43. The internal anatomic dimensions of most humans is such that, if a catheter has the dimensions listed above, and the catheter is inserted so that first marking 43 is located inside the patient's nose and second marking 44 is located outside of the patient's nose, gastric openings 15A-E will be located in the patient's stomach. If the tube is to be inserted via a gastrostomy, first marking 43 is preferably located about 6 inches (15.2 cm) upstream of the most upstream gastric opening 15A. Second marking 44 is preferable located about 4 inches (10.2 cm) further upstream of first marking 43. The internal anatomic dimensions of most humans is such that, if a catheter has the dimensions listed above, and the catheter is inserted via a gastrostomy so that first marking 43 is inside the patient's stomach and second marking 42 is outside the patient, gastric openings 15A-E will be located in the patient's stomach.

In an embodiment of the invention inserted nasally, the catheter has a total length of about 60 inches (152.4 cm). The distance from the furthest downstream gastric opening 15E to the downstream end of the tube 12 is about 21 inches (53.3 cm). The distance between adjacent gastric openings is typically about 1 inch (2.54 cm). When the tube is to be used with a gastrostomy, its overall length is preferably about 38 inches (96.5 cm).

Tube 10 may be approximately 0.180 inches (0.46 cm) in diameter. Suction lumen 25 may be about 0.075 inches (0.19 cm) in diameter. Vent lumen 26 and bolus lumen 27 may each be approximately 0.045 inches (0.11 cm) in diameter. The feeding lumen 28 may be approximately 0.055 inches (0.14 cm) in diameter. Feeding lumen opening 14A may be about 0.5 inches (1.3 cm) from downstream end 12, and feeding lumen opening 14B may be about 0.75 inches (1.9 cm) from downstream end 12. Bolus openings 18A-18B are preferably located about ⅛ inch (0.32 cm) apart.

Figure 8:
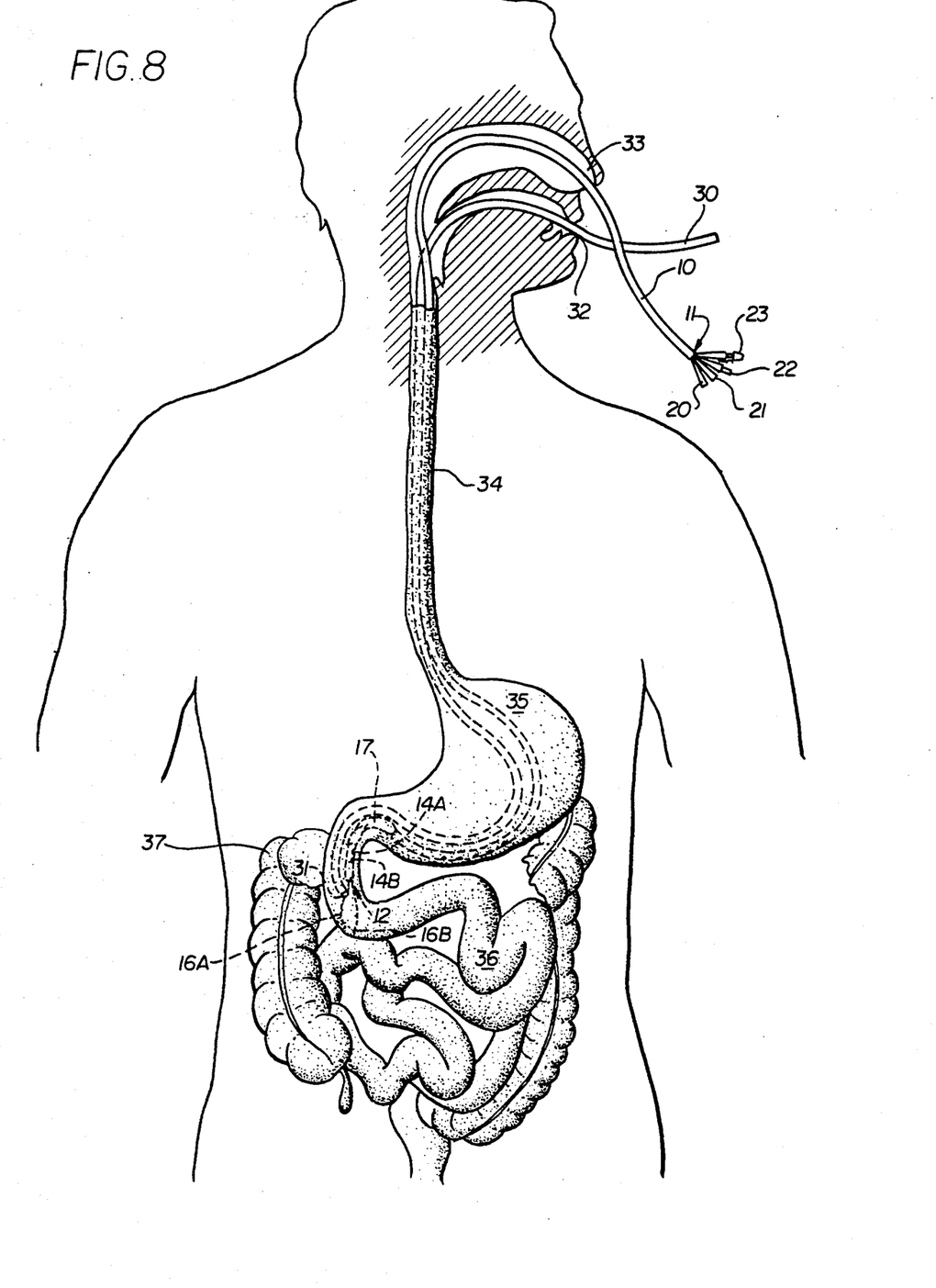
FIG. 8 is a perspective of a human torso, partially cut away, showing a catheter constructed in accordance with the present invention and emplaced further within the gastrointestinal tract through the nose.
Figure 9:
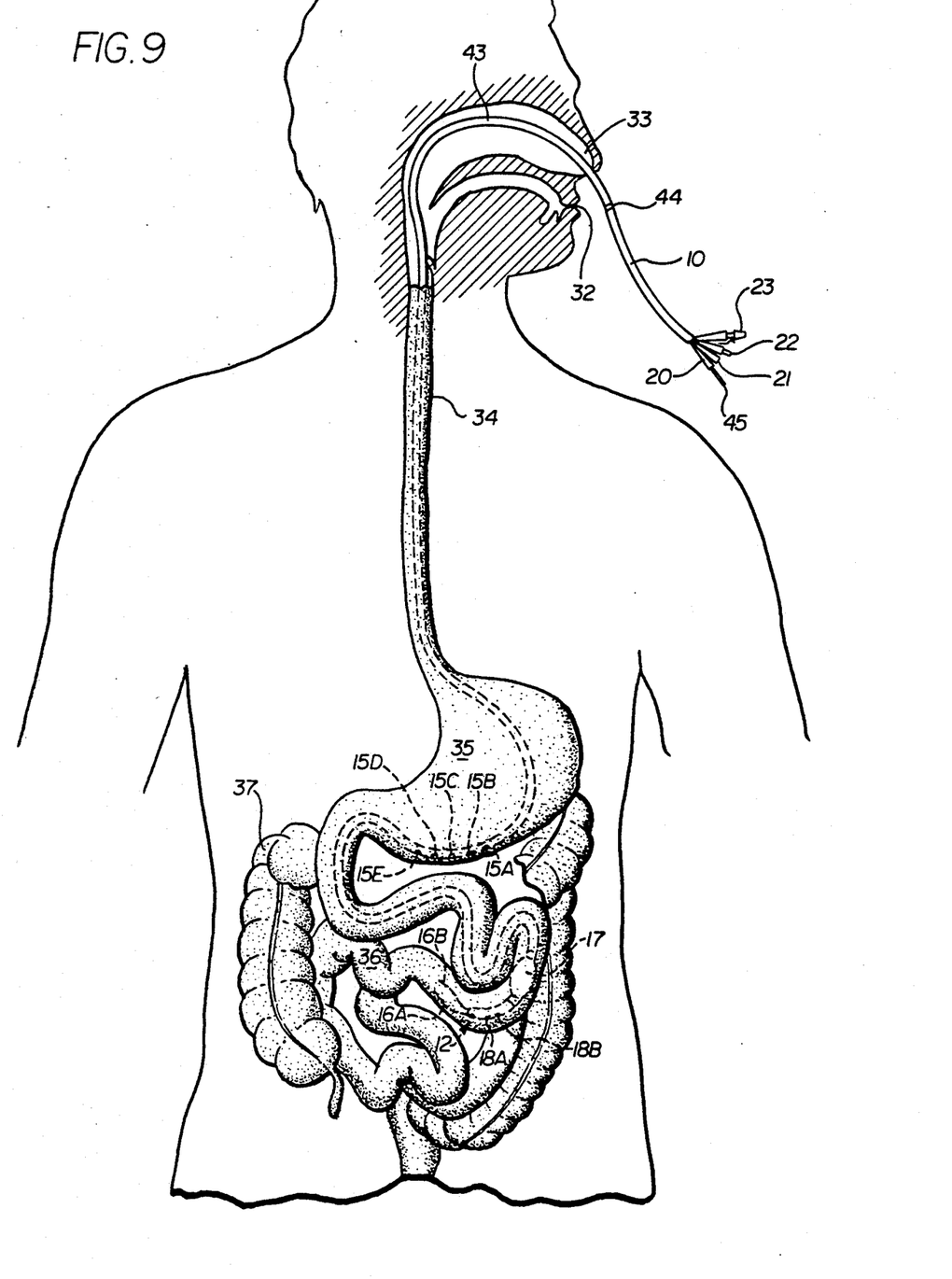
FIG. 9 is a perspective of a human torso, partially cut away, showing a catheter constructed in accordance with the present invention and emplaced still further within the gastrointestinal tract, through the nose.
Figure 10:
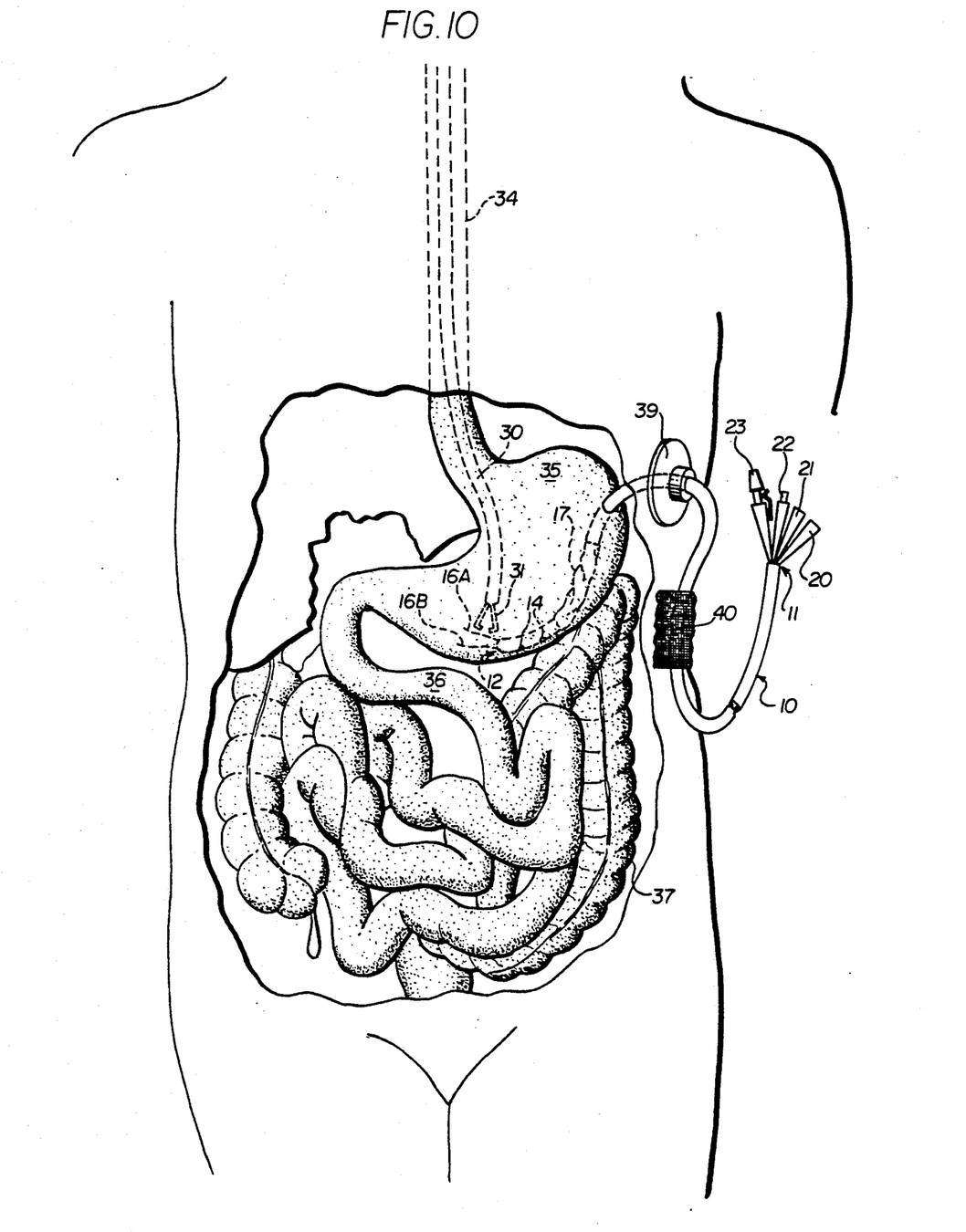
FIG. 10 is a perspective of a human torso, partially cut away, showing a catheter constructed in accordance with the present invention and emplaced within the gastrointestinal tract via a gastrostomy.
Figure 11:
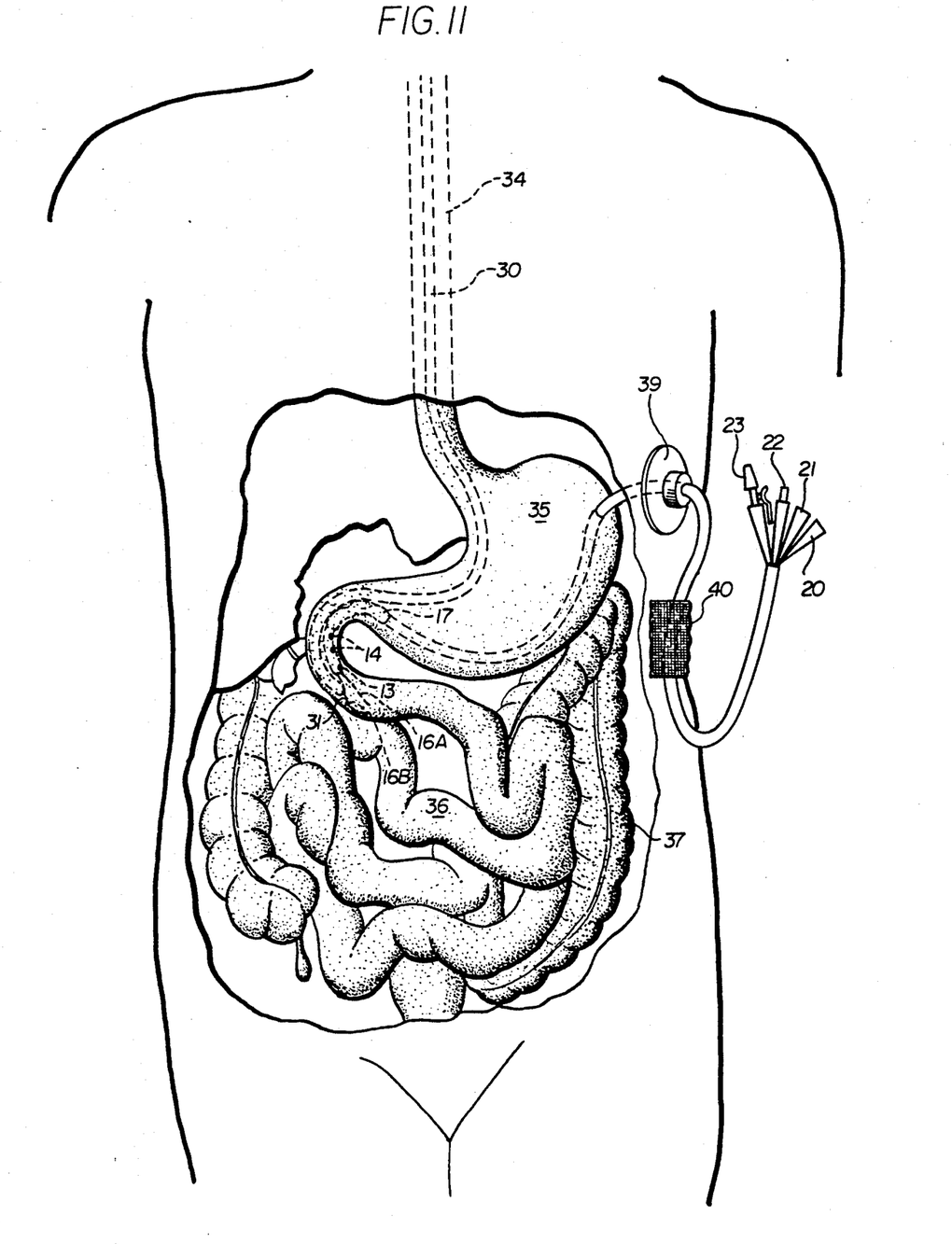
FIG. 11 is a perspective of a human torso, partially cut away, showing a catheter constructed in accordance with the present invention and emplaced further within the gastrointestinal tract, via a gastrostomy.
Figure 12:
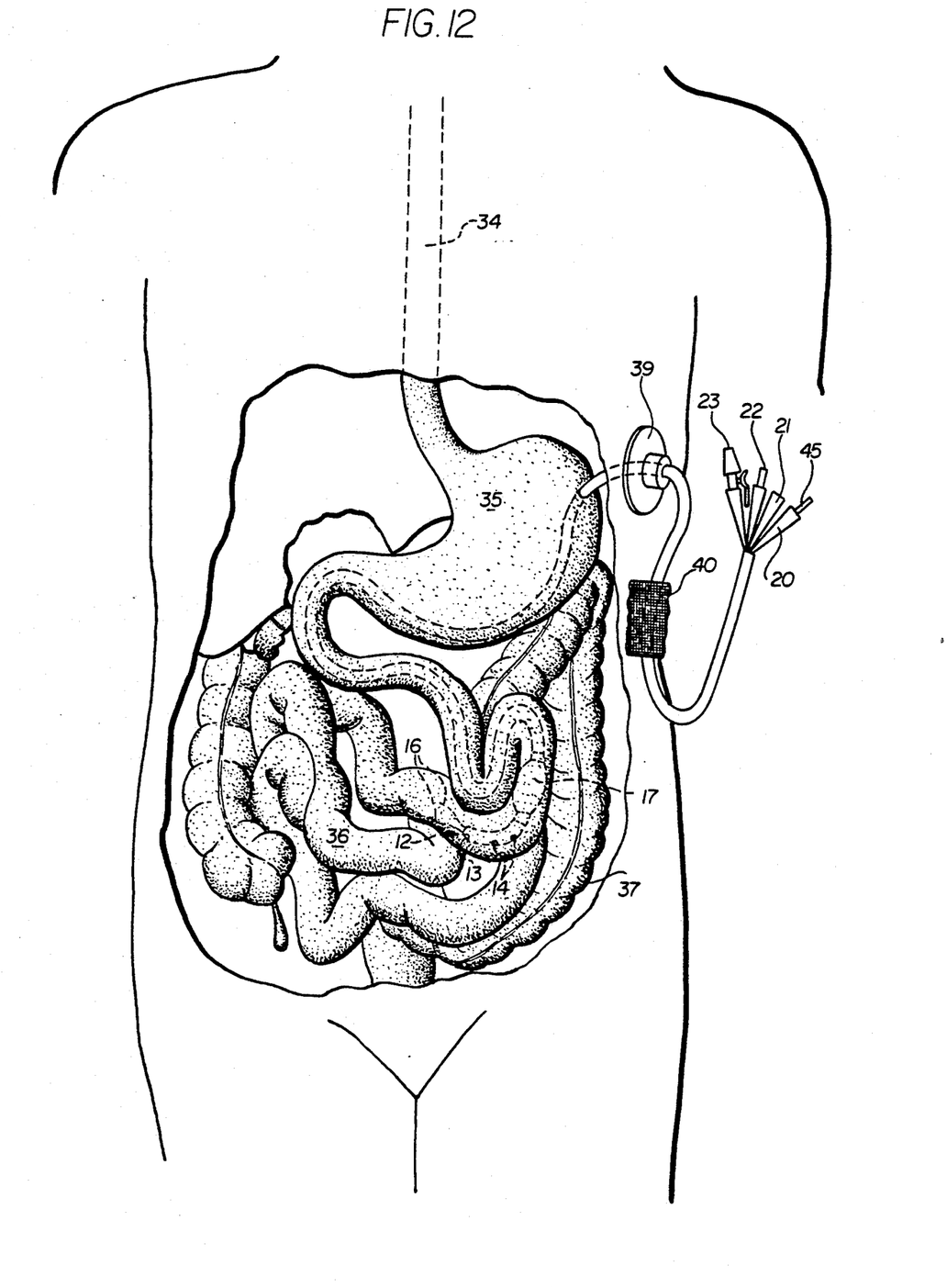
FIG. 12 is a perspective of a human torso, partially cut away, showing a catheter constructed in accordance with the present invention and emplaced still further within the gastrointestinal tract, via a gastrostomy.

FIGS. 7-12 depict catheters, constructed in accordance with embodiments of the present invention, inserted, to varying degrees, into a patient's gastrointestinal tract. The gastrointestinal tract comprises a mouth 32, a nose 33, esophagus 34, stomach 35, small intestine 36 and large intestine 37. FIGS. 7-9 depict use of a nasally inserted gastrointestinal catheter while FIGS. 10-12 depict a catheter inserted via a gastrostomy.

FIG. 7 depicts catheter 10 with downstream end 12 located in stomach 35. Forceps 31 inserted into endoscope 30 are also in the stomach in position to grasp whisker 16A or 16B. Tube 10 has been inserted through nose 33 and esophagus 34, into the stomach 35. In order to place downstream end 12 into the stomach, the catheter can be initially inserted through the nose and into the esophagus where bolus 17 is partially inflated with a liquid such as water. Inflating bolus 17 gives downstream end 12 additional weight so the tube can be swallowed into the stomach.

Once forceps 31 have grasped a whisker, the endoscope pulls tube 10 through stomach 35 and into small intestine 36 (FIG. 8). It may, however, be difficult to maneuver the endoscope and catheter deep into small intestine 36 because of the tight curves in the intestine. At a point where the catheter can no longer be pulled into the intestine by endoscope 30, bolus 17 may be fully inflated by injecting a fluid into bolus fitting 22.

Filling bolus 17 with fluid serves two important functions. First, if the bolus is inflated with a liquid such as water, bolus 17 will have a weight sufficient to enable peristalsis to carry the bolus further into the gastrointestinal tract. Thus the weight of the bolus will aid in insertion of the catheter beyond the point at which endoscopic insertion is no longer feasible. Second, inflating bolus 17 will increase its diameter causing it to engage the intestinal wall. It may be desirable for the bolus to engage the intestinal wall to assist in the prevention of withdrawal of the catheter when the endoscope is removed from the patient.

FIG. 9 depicts the catheter with downstream end 12 at the desired location in small intestine 36. Bolus 17 is shown fully inflated and capable of both engaging the intestinal wall and providing sufficient weight to aid peristalsis in moving it further into the intestinal tract. In FIG. 9, gastric openings 15A–15E are all at the desired location inside stomach 35. First marking 43 is downstream of the entrance to nose 33 and second marking 44 is just upstream or outside of nose 33.

FIG. 10 depicts a catheter of the present invention inserted through a percutaneous gastrostomy and into stomach 35. Tube 10 is inserted through a tube anchor 39 and may be held in place on the skin by tape 40 when the catheter is at the desired location within the gastrointestinal tract. As with nasal insertion, endoscope 30 has forceps 31 which grasp one of the whiskers 16. Tube 10 is pulled downstream by endoscope 30 until downstream end 12 is at the desired location in small intestine 36 or the endoscope can no longer maneuver through the curves of small intestine 36. If the tube cannot be maneuvered further downstream, the bolus may be inflated in a manner similar to a nasal insertion so that peristalsis will move the tube further into small intestine 36 and so that bolus 17 will engage the intestinal wall to assist in the prevention of withdrawal of the tube when the endoscope is removed from the gastrointestinal tract.

Referring to FIGS. 9 and 12, tube 10 may also be inserted into the patient by use of a guidewire 45 which may be inserted through feeding fitting 20 and into feeding lumen 28 for either nasogastric or gastrostomy insertion. The downstream end of guidewire 45 is initially inserted into feeding fitting 20 and through feeding lumen 28 outside of the patient until the downstream end of guidewire 45 is just short of downstream end 12 of tube 10. Then the guidewire and tube are inserted into the patient either nasally or through a gastrostomy. The upstream end of guidewire 45 is then manipulated to move the tube and catheter further into the gastrointestinal tract. As with endoscopic insertion, it may be difficult to maneuver the tube as far into the gastrointestinal tract as is desired. When manipulation further into the small intestine 36 is difficult or impossible, bolus 17 can be inflated with a fluid such as water so that peristalsis will move tube 10 to the desired location.

A catheter of the present invention is capable of either (a) replacing a previously emplaced catheter or (b) being replaced by a new catheter. Once a catheter has been emplaced in the gastrointestinal tract, it may be desirable to remove that catheter and replace it with a new one. In order to replace a catheter, a guidewire can be inserted into the lumen of a previously emplaced catheter through the open upstream end of that catheter and pushed downstream through the lumen. When the downstream end of the guidewire reaches an open downstream end of the lumen in the previously emplaced catheter, the guidewire is held in place, and the previously emplaced catheter is slid over the guidewire and out of the patient's body. In order to slide the earlier emplaced catheter over the guidewire and out of the patient's body, the catheter must, of course, be of the type having an opening at its downstream end much like tip opening 13 of tube 10 in the present invention.

After the earlier catheter has been removed in the manner described in the preceding paragraph, the guidewire will remain emplaced to the same extent downstream within the gastrointestinal tract, as the earlier catheter before that catheter was removed. In order to emplace a new catheter, the end of the guidewire extending outside the patient's body, i.e. the upstream end is inserted through the new catheter's tip opening 13 and into feeding lumen 28. The new catheter is then advanced over the guidewire until the tube's downstream end 12 is at the downstream end of the guidewire, at which time the upstream end of the guidewire should extend out of the feeding connection fitting 20.

If the tube's downstream end 12 is located at a desirable site in the small intestine, the guidewire can be removed through feeding connection fitting 20. If the catheter must be moved further into the gastrointestinal tract, the guidewire should be left in feeding lumen 28. A radiologist can then manipulate the upstream end of the guidewire and catheter, while viewing the catheter and guidewire through a fluoroscope, in the manner conventionally used to advance catheters and guidewires through the gastrointestinal tract.

The above-described replacement procedure can, of course, also be employed with a catheter initially emplaced with the aid of a guidewire and which has not been removed prior to the replacement procedure.

Thus a catheter of the present invention can be used as an aid in inserting other catheters which cannot be properly positioned in the gastrointestinal tract. For instance, it may be desired to emplace a catheter into the intestinal tract which does not have a bolus and cannot be manipulated by use of an endoscope or a guidewire into its desired location. In such an instance, a catheter of the present invention can be emplaced into the gastrointestinal tract by use of an endoscope, or an emplacement guidewire or by inflating the bolus to allow peristalsis to move the catheter to the desired location, and then removed over a removal guidewire. The new tube could then be emplaced into the gastrointestinal tract by means of the method described above where the new catheter has a tip opening that can be slid over the previously emplaced guidewire.

It may be desirable to taper the catheter near its downstream end or to place a bend in the catheter or guidewire near the downstream end of each to aid in the insertion of the tube.

The foregoing detailed description has been given for clearness of understanding only, and no unnecessary limitations should be understood therefrom, as modifications will be obvious to those skilled in the art.

I claim:

1. A catheter for insertion into the small intestine of a patient, said catheter comprising:

a flexible tub having upstream and downstream ends;

a whisker at the downstream end of the tube, said whisker comprising means capable of being grasped by forceps that are attached to an endoscope;

an inflatable bolus near said downstream end and having an interior;

a bolus lumen in said tube;

a bolus opening communicating said bolus lumen with said interior of said bolus;

means, at said upstream end of the tube for connecting said bolus lumen with a source of fluid;
said bolus lumen, said bolus opening and said means for connecting with a source of fluid comprising means for inflating said bolus;
an opening near the downstream end of the tube;
a feeding lumen in said tube, communicating with said opening near the downstream end of the tube, and terminating at the upstream end of the tube;
means, at said upstream end of said feeding lumen, for connecting said feeding lumen to a source of nutritive or medicinal material;
gastric openings, in said flexible tube, between the upstream and downstream ends thereof, for aspirating the stomach;
a suction lumen in said tube, communicating with each gastric opening, and terminating at an upstream end adjacent the upstream end of the tube;
means at said upstream end of said suction lumen for connecting said lumen to suction;
a vent lumen in said tube and terminating at the upstream end of the tube;
a channel connecting said suction lumen to said vent lumen at a location no further upstream than the furthest downstream gastric opening; and
vent means at said upstream end of said vent lumen for communicating said vent lumen to the atmosphere;
said tube having a length such that, when its downstream end is in the small intestine, at least some of said gastric openings are in the stomach, and said channel, said vent lumen and said vent means comprise means for preventing said gastric opening from becoming plugged when aspirating the stomach.

2. The catheter of claim 1 wherein:
said bolus has a center; and
said center is between 1 inch (2.54 cm) and 2 inches (5.08 cm) from said downstream end.

3. The catheter of claim 1 wherein:
said bolus has a length of about 1 inch (2.54 cm).

4. The catheter of claim 1 wherein:
said bolus has a volume such that when the bolus is inflated with water, it has a weight sufficient to enable peristalsis to carry the bolus further into the gastrointestinal tract.

5. The catheter of claim 1 wherein:
said bolus has an inflated diameter which enables the bolus to engage the intestinal wall to assist in the prevention of withdrawal of the tube when an endoscope, which has been inserted in the gastrointestinal tract, is removed therefrom.

6. The catheter of claim 1 wherein:
said tube has a length such that, when the downstream end of the tube is in the small intestine, the upstream end of the tube extends outwardly through the patient's nose.

7. The catheter of claim 1 wherein:
said tube has a length such that when the downstream end of the tube is in the small intestine, the upstream end of the tube extends outwardly through the patient's skin adjacent the stomach.

8. A catheter for insertion into the small intestine of a patient, said catheter comprising:
a flexible tube having upstream and downstream ends;
said tube having an opening in the tip of the downstream end;
a feeding lumen in said tube, communicating with said tip opening near the downstream end of the tube, and terminating at an upstream end adjacent the upstream end of the tube;
means, at said upstream end of said feeding lumen, for connecting said feeding lumen to a source of nutritive or medicinal material;
said feeding lumen comprising means for receiving a guidewire inserted through the feeding lumen's upstream end or through said tip opening in the downstream end of the tube;
a bolus near said downstream end of the tube, said bolus being inflatable and having an interior;
a bolus lumen in said tube;
a bolus opening communicating said bolus lumen with said interior of said bolus;
means, at said upstream end of the tube, for connecting said bolus lumen with a source of fluid;
said bolus lumen, said bolus opening and said means for connecting with a source of fluid comprising means for inflating said bolus;
gastric openings in said tube, between said upstream end and said bolus, for aspirating the stomach;
a suction lumen in said tube, communicating with each gastric opening, and terminating at an upstream end adjacent the upstream end of the tube;
means at said upstream end of said suction lumen for connecting said lumen to suction;
a vent lumen terminating at an upstream end adjacent the upstream end of the tube;
a channel connecting said suction lumen to said vent lumen at a location no further upstream than the furthest downstream gastric opening; and
vent means, at said upstream end of said vent lumen, for communicating said vent lumen to the atmosphere;
said tube having a length such that when its downstream end is in the small intestine, at least some of said gastric openings are in the stomach;
said channel, said vent lumen and said vent means comprising means for preventing said gastric openings from becoming clogged when aspirating the stomach.

9. The catheter of claim 8 wherein:
said bolus has a center; and
said center is between 1 inch (2.54 cm) and 2 inches (5.08 cm) from said downstream end.

10. The catheter of claim 8 wherein:
said bolus has a length of about 1 inch (2.54 cm).

11. The catheter of claim 8 wherein:
said bolus has a volume such that when the bolus is inflated with water, it has a weight sufficient to enable peristalsis to carry said bolus further into the gastrointestinal tract.

12. In combination with the catheter recited in claim 8:
a guidewire;
said guidewire comprising means for emplacing said tube within a patient's gastrointestinal tract.

13. The catheter of claim 12 wherein:
said bolus has an inflated diameter which enables the bolus to engage the intestinal wall to assist in the prevention of withdrawal of the tube when the guidewire is removed from the tube.

14. The catheter of claim 8 wherein:
said tube has a length such that, when the downstream end of the tube is in the small intestine, the upstream end of the tube extends outwardly through the nose.

15. The catheter of claim 8 wherein:
said tube has a length such that, when the downstream end of the tube is in the small intestine, the upstream end of the tube extends outwardly through the patient's skin adjacent the stomach.

16. The catheter of claim 8 and comprising;
a radio-opaque stripe in said tube running from the tube's downstream end to the tube's upstream end.

17. The catheter of claim 8 and comprising:
a radio-opaque area at the downstream end of the tube.

18. A method of replacing (a) a first catheter having upstream and downstream ends, an inflatable bolus near said downstream end, and a tip opening in said downstream end communicating with a feeding lumen communicating with means for connecting said feeding lumen at said upstream end with a source of nutritive or medicinal material with (b) a second catheter having upstream and downstream ends, and a tip opening in said downstream end communicating with a feeding lumen communicating with means for connecting said feeding lumen at said upstream end with a source of nutritive or medicinal material, said method comprising the steps of:

emplacing said first catheter in the gastrointestinal tract;

inserting in said feeding lumen of said first catheter, a guidewire having upstream and downstream ends;

removing said first catheter over said guidewire with said guidewire exiting said first catheter through said tip opening;

inserting the upstream end of said guidewire in said tip opening of said second catheter;

sliding said second catheter over said guidewire while holding said guidewire in place in the patient's gastrointestinal tract;

and removing said guidewire when said downstream end of said second catheter reaches the downstream end of said guidewire.

* * * * *